US011684512B2

(12) United States Patent
Whitsett

(10) Patent No.: US 11,684,512 B2
(45) Date of Patent: Jun. 27, 2023

(54) VITRECTOR AND METHOD FOR PERFORMING A ONE-STEP POSTERIOR VITRECTOMY USING THE SAME

(71) Applicant: Vista Ophthalmics, LLC, Katy, TX (US)

(72) Inventor: Jeffrey Whitsett, Houston, TX (US)

(73) Assignee: Vista Ophthalmics, LLC, Katy, TX (US)

( * ) Notice: Subject to any disclaimer, the term of this patent is extended or adjusted under 35 U.S.C. 154(b) by 254 days.

(21) Appl. No.: 16/812,314

(22) Filed: Mar. 8, 2020

(65) Prior Publication Data

US 2020/0345548 A1 Nov. 5, 2020

Related U.S. Application Data

(60) Provisional application No. 62/843,225, filed on May 3, 2019.

(51) Int. Cl.
*A61F 9/007* (2006.01)
*A61B 17/00* (2006.01)

(52) U.S. Cl.
CPC ........... *A61F 9/00763* (2013.01); *A61B 2017/00544* (2013.01); *A61B 2217/005* (2013.01)

(58) Field of Classification Search
CPC .. A61F 9/00736; A61F 9/00763; A61F 9/007; A61F 9/00709; A61F 9/00745;
(Continued)

(56) References Cited

U.S. PATENT DOCUMENTS 5,716,363 A * 2/1998 Josephberg ......... A61F 9/00763
604/22
8,888,802 B2 11/2014 Underwood et al.
(Continued)

FOREIGN PATENT DOCUMENTS

JP 2015-531266 11/2015
JP 2015531266 11/2015
(Continued)

OTHER PUBLICATIONS

Christopher Nathaniel Roybal, MD, PHD, "Indirect Ophthalmoscopy 101", May 15, 2017, American Academy of Ophthalmology, <https://www.aao.org/young-ophthalmologists/yo-info/article/indirect-ophthalmoscopy-101> (Year: 2017).*
(Continued)

*Primary Examiner* — Darwin P Erezo
*Assistant Examiner* — Christian D. Knauss
(74) *Attorney, Agent, or Firm* — Fish & Richardson P.C.

(57) ABSTRACT

A vitrector for performing a vitrectomy comprises a tubular shaft portion which is attached to a distal end of a vitrector hand piece. The shaft portion is provided with a sharply pointed needle tip portion for piercing the pars plana and sclera of the eye, and a pneumatically driven guillotine cutter is incorporated within the shaft portion of the vitrector at a location immediately adjacent to the sharply pointed needle tip portion. A source of pneumatic air is operatively connected to the proximal end of the vitrector hand piece and is pneumatically connected to the guillotine cutter so as to drive the same. In addition, an aspiration line is also operatively connected to the proximal end of the vitrector hand piece and is also fluidically connected to the region immediately adjacent to the pneumatically driven guillotine cutter so as to remove the floater particles, severed from the
(Continued)

vitreous cavity by means of the pneumatically driven guillotine cutter, by means of aspiration.

20 Claims, 3 Drawing Sheets

(58) Field of Classification Search
CPC .. A61F 9/00754; A61F 2/1662; A61F 2/1664; A61F 2/1667; A61F 2/167; A61F 2/1672; A61F 2/1675; A61F 2/1678
See application file for complete search history.

(56) References Cited

U.S. PATENT DOCUMENTS

| | | | |
|---|---|---|---|
| 9,060,841 B2 | 6/2015 | McCawley | |
| 9,101,442 B2 | 8/2015 | McDonell | |
| 9,498,377 B2 | 11/2016 | McCary et al. | |
| 9,498,378 B2 * | 11/2016 | McDonell | A61F 9/00736 |
| 9,750,639 B2 | 9/2017 | Barnes et al. | |
| 10,376,414 B2 | 8/2019 | Hallen et al. | |
| 2009/0137993 A1 * | 5/2009 | Kurtz | A61F 9/00825 606/6 |
| 2014/0074011 A1 * | 3/2014 | Charles | A61F 9/00745 604/22 |
| 2014/0257257 A1 * | 9/2014 | Grant | A61F 9/00825 606/4 |
| 2016/0166433 A1 | 6/2016 | Czaja | |
| 2018/0311074 A1 | 11/2018 | Heeren | |

FOREIGN PATENT DOCUMENTS

| | | |
|---|---|---|
| JP | 2018-537214 | 12/2018 |
| JP | 20185237214 | 12/2018 |
| WO | WO 2019/069198 | 4/2019 |

OTHER PUBLICATIONS

Ohji et al., "New Instruments in Vitrectomy," Vitreo-retinal Surgery, 2007, 85-98.

* cited by examiner

VITRECTOR AND METHOD FOR PERFORMING A ONE-STEP POSTERIOR VITRECTOMY USING THE SAME

CROSS-REFERENCE TO RELATED PATENT APPLICATION

This United States Non-Provisional Patent Application is a Non-Provisional Perfection of United States Provisional Patent Application, Application No. 62/843,225 which was filed on May 3, 2019 and the priority benefits of which are hereby claimed.

FIELD OF THE INVENTION

The present invention relates generally to medical equipment, and more particularly to a new and improved vitrector and a method for performing a one-step posterior vitrectomy within a patient's eye at the time that cataract surgery has been performed. More particularly, in accordance with the principles and teachings of the present invention, the new and improved vitrector comprises a tubular shaft portion which is attached to a distal end of a vitrector hand piece. In addition, the shaft portion is provided with a sharply pointed needle tip portion for piercing the pars plana and sclera of the eye, and a pneumatically driven guillotine cutter is incorporated within the shaft portion of the vitrector at a location immediately adjacent to the sharply pointed needle tip portion. A source of pneumatic air is operatively connected to the proximal end of the vitrector hand piece and is pneumatically connected to the guillotine cutter so as to drive the same. In addition, an aspiration line is also operatively connected to the proximal end of the vitrector hand piece and is also fluidically connected to the region immediately adjacent to the pneumatically driven guillotine cutter so as to remove the floater particles, severed from the vitreous cavity by means of the pneumatically driven guillotine cutter, by aspiration.

BACKGROUND OF THE INVENTION

Figure 1:
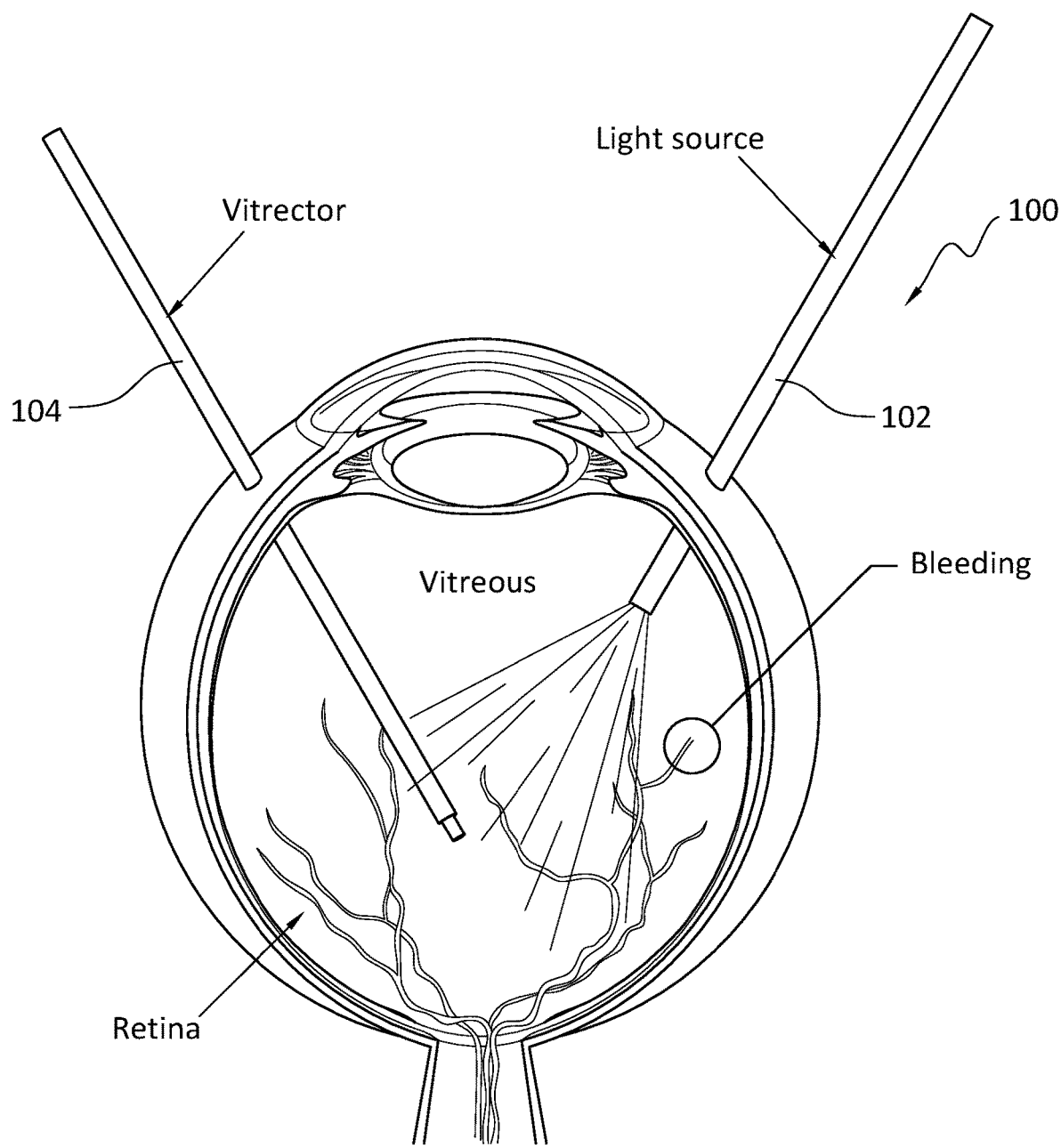

Conventionally, a posterior vitrectomy has been accomplished by means of a three port procedure, in order to remove floaters from the eye, as is generally indicated by the reference character 100 as can be seen in FIG. 1. In order to allow access to the pars plana of the sclera, initially the conjunctiva is incised and folded back so as to expose the sclera and pars plana. Irrigation is initiated by means of a cannula inserted into the eye of the patient through means of a first port formed within the eye by means of an MVR blade so as to maintain physiologic pressure inside the vitreous cavity. This irrigation port is placed and sutured to the sclera, although such is not shown in FIG. 1. Two additional ports are also created through the pars plana by means of an MVR blade so as to allow access for additional instrumentation including a light pipe 102, for visualization, and a pneumatic guillotine cutter for vitreous removal which is incorporated within a conventional, blunt-tipped vitrector 104. After the procedure, the entry sites are closed with absorbable sutures so as to maintain water-tight integrity of the vitreous cavity. As can be readily appreciated, however, this conventional technique is time-consuming, comprises multiple steps and implements or equipment, and can be bothersome to the patient.

A need therefore exists in the art for a new and improved vitrector and a method for performing a vitrectomy. Another need exists in the art for a new and improved vitrector and a method for performing a vitrectomy wherein the entire procedure can be radically simplified. Still another need exists in the art for a new and improved vitrector and a method for performing a vitrectomy wherein the entire procedure can be radically simplified, can be significantly shortened in duration, and can be less bothersome to the patient. Yet another need exists in the art for a new and improved vitrector and a method for performing a vitrectomy wherein the entire procedure is radically simplified, can be significantly shortened in duration, and can be less bothersome to the patient. Yet still another need exists in the art for a new and improved vitrector and a method for performing a vitrectomy wherein the entire procedure is radically simplified, can be significantly shortened, and can be less bothersome to the patient as a result of reducing the number of incisions that need to be made within or through various regions of the eye. A further need exists in the art for a new and improved vitrector and a method for performing a vitrectomy wherein the entire procedure is radically simplified, can be significantly shortened, and can be less bothersome to the patient as a result of reducing the number of incisions that need to be made within or through various regions of the eye in order to accommodate the various different medical instruments or components currently required to perform a conventional vitrectomy.

OVERALL OBJECTIVES OF THE INVENTION

Therefore, an overall objective of the present invention is to provide a new and improved vitrector and a method for performing a vitrectomy. Another overall objective of the present invention is to provide a new and improved vitrector and a method for performing a vitrectomy wherein the entire procedure can be radically simplified. Still another overall objective of the present invention is to provide a new and improved vitrector and a method for performing a vitrectomy wherein the entire procedure can be radically simplified, can be significantly shortened in duration, and can be less bothersome to the patient. Yet another overall objective of the present invention is to provide a new and improved vitrector and a method for performing a vitrectomy wherein the entire procedure is radically simplified, can be significantly shortened in duration, and can be less bothersome to the patient. Yet still another overall objective of the present invention is to provide a new and improved vitrector and a method for performing a vitrectomy wherein the entire procedure is radically simplified, can be significantly shortened, and can be less bothersome to the patient as a result of reducing the number of incisions that need to be made within or through various regions of the eye. A further overall objective of the present invention is to provide a new and improved vitrector and a method for performing a vitrectomy wherein the entire procedure is radically simplified, can be significantly shortened, and can be less bothersome to the patient as a result of reducing the number of incisions that need to be made within or through various regions of the eye in order to accommodate the various different medical instruments or components currently required to perform a conventional vitrectomy.

SUMMARY OF THE INVENTION

Briefly, the present invention comprises the development of a one step vitrector is an advancement in the art in providing access to the anterior and mid vitreous debris, but even more importantly, the significant improvement is that it can be easily performed by the anterior segment surgeon at the time of cataract surgery. Floaters occur over time as the process of vitreous aging (syneresis) changes the dynamics in the vitreous cavity. As this process occurs, the syneretic vitreous places pressure upon posterior vitreous attachments, causing them to break free and subsequently lodge within the anterior/mid vitreous. These floaters can range in size from small and visually insignificant, to large and visually quite distracting. Classic management of this condition has been observation, with natural adaptation and the long term break down of the floater. Oftentimes, patients have to move their eye to shift the floater while performing simple activities as driving and reading. The ability to remove significant floaters at the time of cataract surgery will allow the patient to have visual improvement with minimal if any additional surgical time and morbidity.

In accordance with the principles and teachings of the present invention, the new and improved vitrector comprises a tubular shaft portion which is attached to a distal end of a vitrector hand piece. In addition, the shaft portion is provided with a sharply pointed needle tip portion for piercing the pars plana and sclera of the eye, and a pneumatically driven guillotine cutter is incorporated within the shaft portion of the vitrector at a location immediately adjacent to the sharply pointed needle tip portion. A source of pneumatic air is operatively connected to the proximal end of the vitrector hand piece and is pneumatically connected to the guillotine cutter so as to drive the same. In addition, an aspiration line is also operatively connected to the proximal end of the vitrector hand piece and is also fluidically connected to the region immediately adjacent to the pneumatically driven guillotine cutter so as to remove the floater particles, severed from the vitreous cavity by means of the pneumatically driven guillotine cutter, by aspiration.

BRIEF DESCRIPTIONS OF THE DRAWINGS

Figure 2:
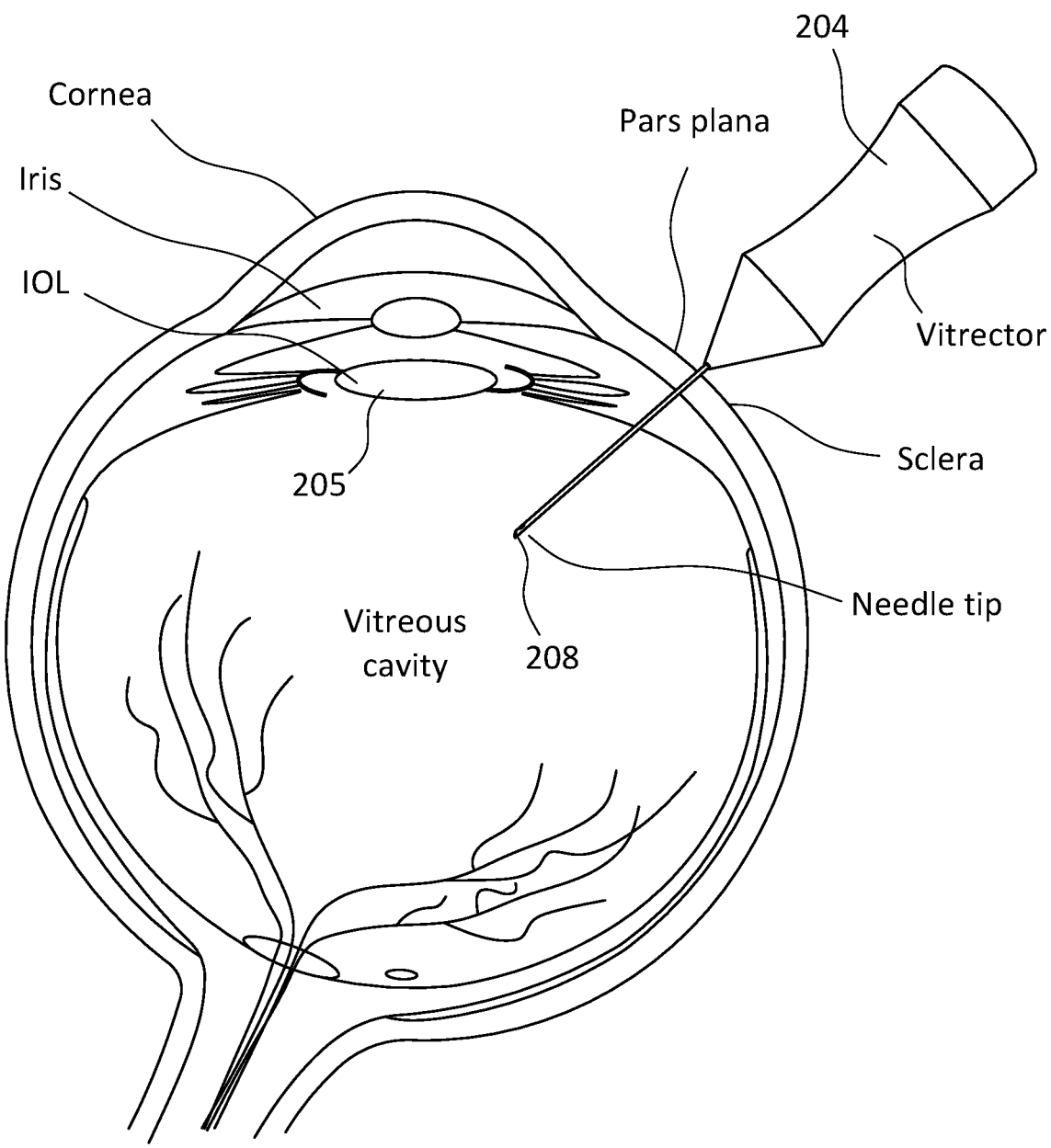
Figure 3:
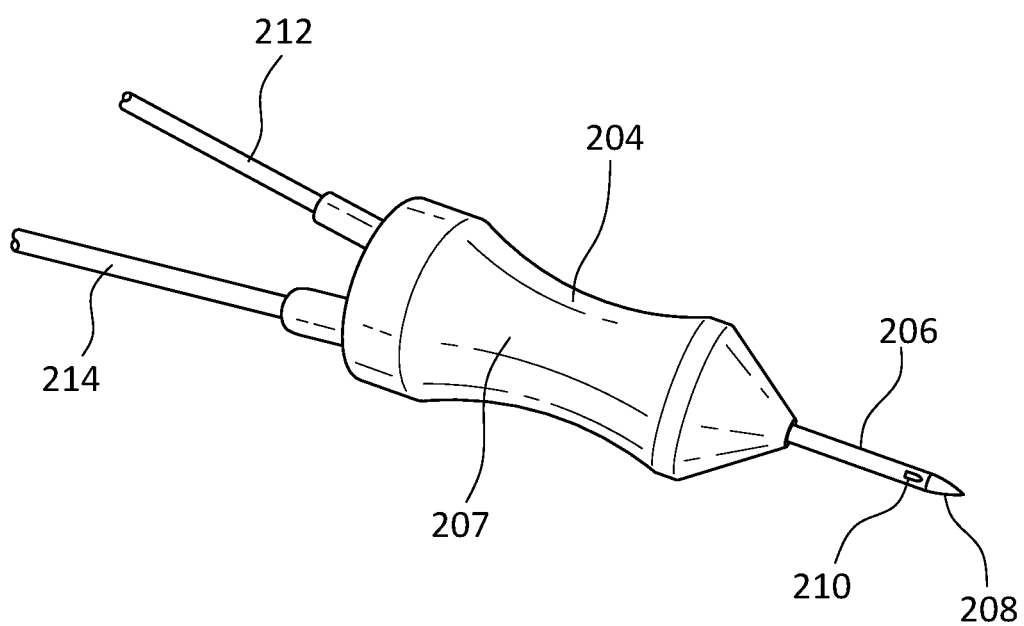

Various other features and attendant advantages of the present invention will be more fully appreciated from the following detailed description when considered in connection with the accompanying drawings in which like reference characters designate like or corresponding parts throughout the several views, and wherein:

FIG. 1 is a schematic cross-sectional view of the human eye wherein a conventional, PRIOR ART system of medical instruments and other components are utilized in order to perform a conventional vitrectomy;

FIG. 2 is a schematic cross-sectional view of the human eye, and is similar to that of FIG. 1 illustrating, however, how a vitrectomy is performed utilizing the new and improved vitrector of the present invention and in accordance with the new and improved method of performing a vitrectomy; and FIG. 3 is a schematic view of the new and improved vitrector of the present invention illustrating the various components thereof.

DETAILED DESCRIPTION OF THE PRESENT INVENTION

Before proceeding with the detailed description of the present invention, it may be helpful to initially understand several medical terms which relate to the various regions of the eye in connection with which a vitrectomy is to be performed by means of the cataract surgeon, whereby the performance of the vitrectomy will be better understood:

For example, the VITREOUS comprises a transparent colorless gel that fills the posterior chamber of the eye. The vitreous is composed of water, collagen and hyaluronic acid.

FLOATERS are spots in your vision that are lodged within the vitreous. Most eye floaters occur as a result of an aging phenomenon wherein the gel fluid changes over time. Microscopic fibers congeal and become lodged within the vitreous gel. If located centrally, they can cast shadows upon the retina and thereby cause obstructions to one's vision.

POSTERIOR VITREOUS DETACHMENT is a naturally occurring process wherein, as the vitreous gel changes, the attachment to the eye becomes detached and moves into the vitreous cavity.

The SCLERA comprises the outer covering of the eyeball which is composed of collagen and elastic fibers.

The CORNEA comprises the transparent layer that covers the front part of the eye. The primary function of the cornea is to refract or bend light.

A VITRECTOMY is a surgical procedure which removes vitreous gel and other functional abnormalities through a small port system incised into the eyeball.

The VISCOELASTIC is a clear viscous substance comprised of sodium hyaluronate which is used in ocular surgery to maintain space, and to protect ocular structures.

An IOL is an intraocular lens, an artificial lens, which is implanted at the time of cataract surgery so as to help bend light and focus it upon the retina. An IOL replaces one's original lens when, due to aging, the original lens becomes cloudy or progressively opaque, thereby rendering normal vision virtually impossible and not correctable by means of glasses, contact lenses, or the like.

VITREOUS SYNERESIS is a naturally occurring process, as we age, in which the composition of the vitreous cavity changes so that its content comprises a greater percentage of water content. It is generally a precursor of posterior vitreous detachment.

The PARS PLANA is an area of the sclera, approximately 3-4 mm posterior to the surgical limbus and a common entry site for the entry or insertion of surgical instruments into the posterior vitreous.

Having described the problems or difficulties encountered in connection with the performance of a conventional vitrectomy, and having further defined the various regions of the eye, the various conditions that can affect the eye, it is time to fully disclose the vitrector of the present invention. In accordance with the principles and teachings of the present invention, and as disclosed within FIGS. 2 and 3, cataract surgery is performed in the usual manner, and after the intraocular lens (IOL) is implanted, the cohesive viscoelastic is refilled or retained within the anterior chamber. The primary incision and the paracentesis are hydrated so as to prevent the collapse of the anterior chamber while the one-step vitrectomy is performed. Adequate dilation is mandatory for the procedure as it is important to visualize the tip and one-step cutter at all times. After the anterior chamber is refilled with viscoelastic material, a caliper is used to measure 3-3.5 mm posterior to the surgical limbus. Using counter-traction, the one step vitrector 204 is inserted through the conjunctiva and pars plana, and into the vitreous cavity with the tip aimed toward the mid vitreous, under constant visualization, behind the the intraocular lens (IOL) 205. This is the location where the anterior and mid vitreous floaters will be located and removed.

As can best be seen or appreciated from FIG. 3, in addition to FIG. 2, and in lieu of the conventional, prior art vitrector, which has a blunt tip or end portion, the new and improved vitrector 204 comprises a tubular shaft portion 206 which is approximately 27 gauge in diameter and approximately one half inch (0.5000") to nine-sixteenths of an inch (0.5625") in length such that the tubular shaft portion 206 has the inherent stiffness required for the procedure. The shaft portion 206 is attached to the distal end portion of a vitrector hand piece 207. In addition, the shaft portion 206 is provided with a sharply pointed needle tip portion 208 for piercing the pars plana and sclera of the eye, and a pneumatically driven guillotine cutter 210 is incorporated within the shaft portion 206 of the vitrector 204 immediately adjacent to the sharply pointed needle tip portion 208.

A source of pneumatic air 212 is operatively connected to the proximal end of the vitrector hand piece 207 and is adapted to be fluidically connected to the pneumatically driven guillotine cutter 210 so as to drive the same. In a similar manner, an aspiration line 214 is also operatively connected to the proximal end of the vitrector hand piece 207 and is also fluidically connected to the region immediately adjacent to the pneumatically driven guillotine cutter 210 so as to remove the floater particles, which are severed from the vitreous cavity by means of the pneumatically driven guillotine cutter 210, by means of aspiration. After adequate removal under visualization, the vitrector 204 is removed and gentle pressure is applied with a cotton tip applicator. The viscoelastic is then removed from the anterior chamber in the usual fashion, whereby the pressure within the anterior chamber is restored to its normal physiological level using a balanced saline solution.

It is lastly noted that no additional illumination is required in view of the fact that the anterior vitreous can be easily visualized through the dilated pupil of the eye and the intraocular lens (IOL) 205.

Obviously, many variations and modifications of the present invention are possible in light of the above teachings. It is therefore to be understood that within the scope of the appended claims, the present invention may be practiced otherwise than as specifically described herein.

REFERENCE NUMBER KEY

100—Conventional, prior art vitrector system
102—Light pipe of vitrector system 100
104—Conventional vitrector
204—Vitrector of present invention
205—Intraocular lens
206—Shaft of vitrector 204
207—Hand piece of vitrector 204
208—Sharp pointed tip portion of vitrector 204
210—Pneumatically driven guillotine cutter
212—Pneumatic line for fluidically driving guillotine cutter 201
214—Aspiration line for aspirationally removing floaters from the vitreous humor

What is claimed, and is desired to be protected by Letters Patent, is:

1. A surgical procedure comprising:
   performing a cataract surgery on an eye; and
   during the cataract surgery and after implanting an intraocular lens in the eye, performing a method to remove one or more floaters from a vitreous portion of the eye, the method comprising:
   visualizing the vitreous portion of the eye through a dilated pupil of the eye and the intraocular lens of the eye without inserting a separate light source into the eye; and
   while visualizing the vitreous portion of the eye:
   forming a single insertion entry port through a pars plana and a sclera of the eye using a vitrector comprising a hand piece, a shaft fixedly attached at a first end thereof to a first end of the hand piece, and a sharply pointed needle tip fixedly connected to a second end of the shaft for piercing the pars plana and sclera of the eye;
   pneumatically driving a pneumatically driven guillotine cutter incorporated within the shaft to sever the one or more floaters from the vitreous portion of the eye; and
   aspirating the one or more severed floaters from the eye.

2. The method of claim 1, further comprising:
   operatively connecting a source of pneumatic air to a second end of the hand piece such that the source of pneumatic air is pneumatically connected to the pneumatically driven guillotine cutter.

3. The method of claim 1, further comprising:
   fluidically connecting an aspiration line to the pneumatically driven guillotine cutter for aspirationally removing the one or more floaters severed from the vitreous portion of the eye by the pneumatically driven guillotine cutter.

4. The method of claim 3, further comprising:
   operatively connecting the aspiration line to a second end of the hand piece such that the aspiration line is fluidically connected to the pneumatically driven guillotine cutter.

5. The method of claim 1, further comprising:
   prior to pneumatically driving the pneumatically driven guillotine cutter, positioning the needle tip in a mid-vitreous portion of the eye.

6. The method of claim 5, wherein positioning the needle tip in the mid-vitreous portion of the eye comprises positioning the needle tip behind the intraocular lens implanted in the eye.

7. The method of claim 5, wherein positioning the needle tip in the mid-vitreous portion of the eye comprises passing the needle tip through the pars plana and conjunctiva of the eye.

8. The method of claim 1, further comprising:
   removing the needle tip from the eye; and
   removing a viscoelastic fluid from an anterior chamber of the eye.

9. The method of claim 8, further comprising, after removing the needle tip from the eye, infusing a saline solution into the anterior chamber to restore a pressure within the anterior chamber to a normal physiological level.

10. The method of claim 1, wherein the shaft has a length of between 0.5 inches and 0.5625 inches.

11. The method of claim 1, wherein the shaft has a 27 gauge diameter.

12. The method of claim 1, further comprising:
    after implanting the intraocular lens in the eye and prior to forming the single insertion entry port through the pars plana and the sclera of the eye using the vitrector, filling an anterior chamber of the eye with a viscoelastic fluid.

13. A surgical procedure comprising:
performing a cataract surgery on an eye, the cataract surgery comprising:
  implanting an intraocular lens in the eye; and
  during the cataract surgery and after implanting the intraocular lens in the eye, performing a method to remove one or more floaters from a vitreous portion of the eye, the method comprising:
    filling an anterior chamber of the eye with viscoelastic fluid;
    hydrating an incision formed in the eye during implantation of the intraocular lens with fluid;
    visualizing the vitreous portion of the eye through a dilated pupil of the eye and the intraocular lens of the eye without inserting a separate light source into the eye; and
    while visualizing the vitreous portion of the eye:
      measuring a distance 3 mm to 3.5 mm posterior to a surgical limbus of the eye;
      forming a single insertion entry port through a pars plana and a sclera of the eye using a vitrector comprising a hand piece, a shaft fixedly attached at a first end thereof to a first end of the hand piece, and a sharply pointed needle tip fixedly connected to a second end of the shaft for piercing the pars plana and sclera of the eye;
      based on the measurement, positioning the needle tip of the vitrector in an anterior or mid-vitreous portion of the eye;
      pneumatically driving a pneumatically driven guillotine cutter incorporated within the shaft to sever the one or more floaters from the vitreous portion of the eye; and
      aspirating the one or more severed floaters from the eye;
      removing the vitrector from the eye;
      removing the viscoelastic fluid from the anterior chamber of the eye; and
      following removal of the vitrector from the eye, infusing the eye with a saline solution.

14. The method of claim 13, further comprising:
operatively connecting a source of pneumatic air to a second end of the hand piece such that the source of pneumatic air is pneumatically connected to the pneumatically driven guillotine cutter.

15. The method of claim 13, further comprising:
fluidically connecting an aspiration line to the pneumatically driven guillotine cutter for aspirationally removing the one or more floaters severed from the vitreous portion of the eye by the pneumatically driven guillotine cutter.

16. The method of claim 13, wherein positioning the needle tip of the vitrector in the anterior or mid-vitreous portion of the eye comprises positioning the needle tip behind the intraocular lens implanted in the eye.

17. The method of claim 13, wherein positioning the needle tip of the vitrector in the anterior or mid-vitreous portion of the eye comprises passing the needle tip through the pars plana and conjunctiva of the eye.

18. The method of claim 13, wherein the shaft has a length of between 0.5 inches and 0.5625 inches.

19. The method of claim 13, wherein the shaft has a 27 gauge diameter.

20. The method of claim 13, wherein filling the anterior chamber of the eye with viscoelastic fluid comprises refilling the anterior chamber with viscoelastic fluid.

* * * * *